United States Patent [19]
Chichester et al.

[11] Patent Number: 5,982,499
[45] Date of Patent: Nov. 9, 1999

[54] HIGH THROUGHPUT PHOTOREFLECTANCE TECHNIQUE AND APPARATUS

[75] Inventors: Robert J. Chichester, Somerville, N.J.; Harald F. Hess, San Diego, Calif.

[73] Assignee: Lucent Technologies Inc., Murray Hill, N.J.

[21] Appl. No.: 09/024,603

[22] Filed: Feb. 17, 1998

[51] Int. Cl.[6] ................................................. G01N 21/55
[52] U.S. Cl. .......................... 356/445; 356/417; 356/432
[58] Field of Search .................................... 356/417, 432, 356/445

[56] References Cited

U.S. PATENT DOCUMENTS

| | | | |
|---|---|---|---|
| 5,255,070 | 10/1993 | Pollack et al. | 356/417 |
| 5,255,071 | 10/1993 | Pollack et al. | 356/417 |
| 5,260,772 | 11/1993 | Pollack et al. | 356/417 |
| 5,270,797 | 12/1993 | Pollak et al. | 356/417 |
| 5,287,169 | 2/1994 | Pollack et al. | 356/445 |

*Primary Examiner*—Robert H. Kim
*Attorney, Agent, or Firm*—E. E. Pacher

[57] ABSTRACT

A plurality of PR measurements are simultaneously made at N different spots on a wafer by forming N modulated pump beams and N tunable probe beams, and directing one pump beam and one probe beam so as to form overlapping images at each of the N spots. Each of a like plurality of N photodetectors receives a portion of the corresponding probe beam which is reflected from the surface of the wafer to provide information about the wafer characteristics at each spot. In one embodiment, automatic alignment of the probe and pump beams along a row of N spots is achieved by means of a semi-cylindrical scan head which has an axial cavity overlapping the row of N spots and a plurality of radial cavities organized into separate, but interleaved input and output groups. The cavities of two separate input groups receive optical fibers carrying the probe and pump beams to the row of N spots. The cavities of two separate output groups receive photodetectors for detecting the reflected beam and for monitoring the pump beam. The scan head and/or the wafer are moved relative to one another in order to make measurements at various row locations on the wafer (e.g., to map the wafer).

15 Claims, 3 Drawing Sheets

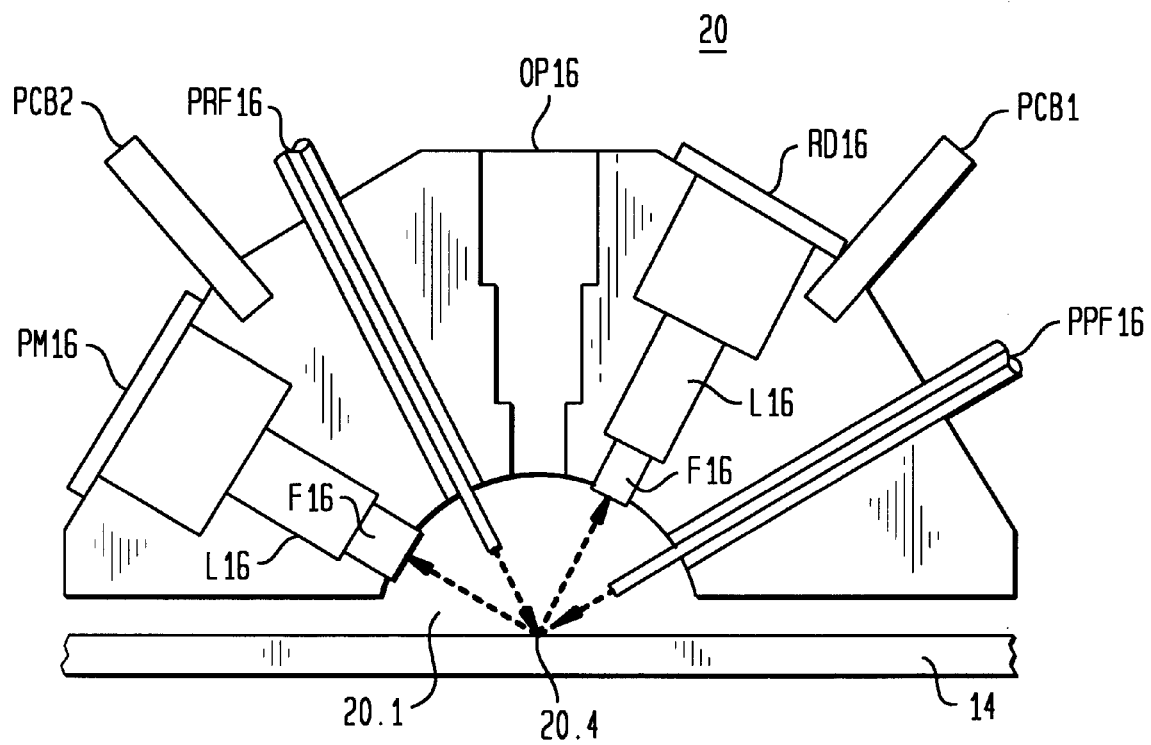

HIGH THROUGHPUT PHOTOREFLECTANCE TECHNIQUE AND APPARATUS

FIELD OF THE INVENTION

This invention relates generally to optical techniques for determining a material's characteristics and, more particularly, to photoreflectance (PR) techniques that enable improved throughout in characterizing the properties of semiconductor wafers.

BACKGROUND OF THE INVENTION

In PR techniques a pump beam and a probe beam are simultaneously directed at a small spot on a semiconductor wafer. The pump beam, which is absorbed in the semiconductor and is chopped at a relatively slow frequency, generates electron-hole pairs which modulate the built-in electric field of the semiconductor material. The probe beam is reflected from the wafer surface, and the reflected signal is detected to provide information about the material's characteristics. According to F. H. Pollack et al., PR has been known for more than 20 years, but interest in it has been diminished by experimental difficulties including scattered light from the pump beam and photoluminescence from the wafer. Pollack et al. describe computerized procedures to improve the signal-to-noise ratio and gain additional information on the materials examined. In this regard, see the family of F. H. Pollack et al. U.S. Pat. Nos. including 5,260,772 (issued on Nov. 9, 1993), 5,270,797 (issued on Dec. 14, 1993), 5,255,070 (issued on Oct. 19, 1993), 5,255,071 (issued on Oct. 19, 1997) and 5,287,169 (issued on Feb. 15, 1994), all of which are incorporated herein by reference.

The prior art procedures implementing such PR techniques have been slow and cumbersome, entailing measurements made at only one small spot at a time on a wafer. Each such measurement typically consumes 15–30 minutes. Thus, it could take 50–100 hours to make several hundred PR measurements on even a relatively small 2-inch diameter wafer (as would done to map the entire wafer). Of course, mapping of even larger wafers would take commensurately longer.

Thus, a need remains in the art for a PR technique which improves throughput by enabling multiple measurements, and hence wafer mapping, to be performed more rapidly.

SUMMARY OF THE INVENTION

In accordance with one aspect of our invention, a plurality of PR measurements are simultaneously made at N different spots on a wafer by forming N modulated pump beams and N tunable probe beams, and directing one such pump beam and one such probe beam simultaneously at each of the N spots. Each of a like plurality of N photodetectors receives a portion of the corresponding probe beam which is reflected from the surface of the wafer to provide information about the wafer characteristics at each spot.

In accordance with another aspect of our invention, automatic alignment of the probe and pump beams along a row of N spots is achieved by means of a semi-cylindrical scan head which has an axial cavity overlapping the row of N spots and a plurality of radial cavities organized into separate, but interleaved input and output groups. The cavities of two separate input groups receive optical fibers carrying the probe and pump beams to the row of N spots. The cavities of two separate output groups receive photodetectors for detecting the reflected beam and for monitoring the pump beam. The scan head and/or the wafer are moved relative to one another in order to make measurements at various row locations on the wafer (e.g., to map the wafer).

BRIEF DESCRIPTION OF THE DRAWINGS

Our invention, together with its various features and advantages, can be readily understood from the following more detailed description taken in conjunction with the accompanying drawing, in which:

FIG. 5 is similar to FIG. 3 but with various components inserted into the radial cavities.

In the interests of clarity and simplicity, the figures have not been drawn to scale. In addition, when describing physical or optical dimensions, the symbol A stands for Angstroms.

DETAILED DESCRIPTION OF THE INVENTION

Figure 1:
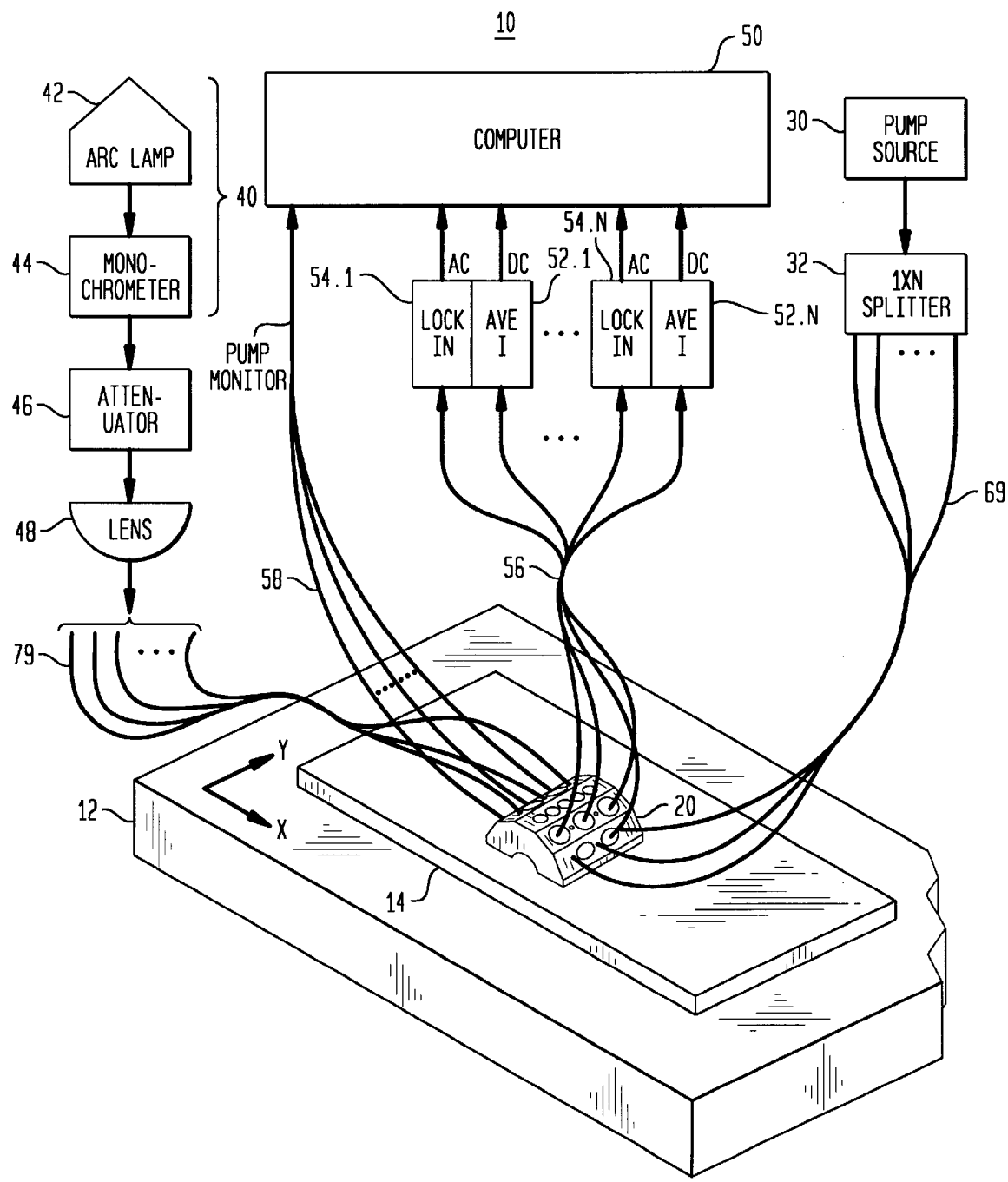
FIG. 1 is a partial block diagrammatic, partial isometric view of apparatus for making PR measurements simultaneously at multiple spots on a wafer in accordance with one aspect of our invention.

With reference now to FIG. 1, apparatus 10 for making PR measurements on a semiconductor wafer 14 includes a translatable table 12 which supports the wafer and a scan head 20 positioned above the wafer. In order for the head 20 to scan the wafer 14, the head and/or the wafer are moved relative to one another. For purpose of illustration only, FIG. 1 shows an embodiment in which the scan head 20 is fixed and the wafer is moved by means of the translatable table in the x-y plane. In the interests of simplicity, the fixture holding the scan head above the wafer surface has been omitted.

In addition, although the wafer 14 is depicted as being much larger than the scan head, in some cases the wafer and the scan head may be of similar size. The latter situation might occur, for example, with Group III–V compound wafers which are typically only 2–3 inches in diameter. In such cases, the scan head may be long enough to cover all of the desired spots in the y-direction, making it sufficient to translate the wafer in only the x-direction, rather than in both directions.

In accordance with one aspect of our invention, a plurality of PR measurements are simultaneously made at N different spots on wafer 14 by forming N modulated pump beams and N tunable probe beams, and by directing one such pump beam and one such probe beam simultaneously at each of the N spots. Each pump beam and its corresponding probe beam are imaged onto one of the N spots. The beam images overlap on the wafer surface and, preferably, the pump beam image is at least as large as the probe beam image. Illustratively, these images are 400–600 $\mu$m in size, and their shapes are roughly elliptical. Alternatively, it may be advantageous in some applications (e.g., where finer grained information is desired) to use a probe beam image which is much smaller (e.g., 10 $\mu$m in size) than the pump beam image (e.g., 500 $\mu$m in size).

Each of a like plurality of N photodetectors receives a portion of the corresponding probe beam which is reflected from the surface of the wafer to provide information about the wafer characteristics. More specifically, the output of a modulated pump source 30 (e.g., an electro-absorption modulated (EML) semiconductor laser) is split into N pump signals by a conventional 1×N splitter 32 and delivered to the scan head 20, and hence to the row of N spots on wafer 14, by means of optical fibers 69. Likewise, the slit-shaped output of a wavelength tunable probe source 40 (e.g., a tunable laser, or, as shown, the combination of an arc lamp 42 and a monochromator 44) is passed through an attenuator 46 to a lens 48. The lens images the output of the monochromator slit onto a linear array of the ends of N optical fibers 79. Thus, the fibers 79 deliver N probe beams to the scan head 20, and hence to the row of N spots on the wafer 14.

The portion of the probe beam reflected from each spot contains information about the wafer material and/or structure at that spot. N such reflected beams are detected by a like number of photodetectors (e.g., RD16 of FIG. 5) which deliver N electrical signals to N lock-in amplifiers $54n$ (n=1,2 . . . N) and N passive R-C networks $52n$ (n=1,2 . . . N) by means of cable 56. The former separates out the AC component of the reflected signal, whereas the latter separates out the corresponding DC component, as is well known in the art. Both components are supplied as inputs to computer 50 which analyzes the inputs and calculates various parameters characteristic of the wafer material and/or structure.

Another set of N photodetectors (e.g., PM16 of FIG. 5) monitors the intensity of the N pump beams and delivers N corresponding electrical signals to computer 50 by means of cable 58.

In accordance with one embodiment of our invention, the scan head 20 enables PR measurements to be made simultaneously at a row of N spots on the wafer 14 while automatically aligning the N pump beams and the N probe beams to the row of N spots, thereby significantly increasing throughput. As shown in greater detail in FIGS. 2–5 for the illustrative case of N=16, the scan head 20 comprises a semi-cylindrical body having an axial cavity 20.1, the central axis of which overlays the row of 16 spots (e.g., spot 20.4 of FIG. 5). The scan head body also has a plurality of radial cavities $39n$ and $49n$ (n=1,2 . . . 16) which communicate between the exterior of the scan head and the axial cavity 20.1. The radial cavities include a group of observation ports OP$n$ (n=1,2 . . . 16) as well as interleaved groups of input ports $39n$, $49n$ (n=1,2 . . . 16) and output ports D$n$, M$n$ (n=1,2 . . . 16). The scan head illustratively has five axial facets 20a–20f in which the various ports are formed. Thus, in one embodiment the observation ports OP$n$ are formed in the top facet 20c, whereas the input and output ports are formed in the lateral facets 20a, 20b, 20d and 20e. The input ports $39n$, $49n$ have smaller diameters than the output ports D$n$, M$n$ inasmuch as each of the former is adapted to receive an optical fiber (e.g., pump fiber PPF16 or probe fiber PRF 16 of FIG. 5), whereas each of the latter is adapted to receive a photodetector (e.g., reflected signal detector RD16 or pump monitor PM16 of FIG. 5).

Figure 2:
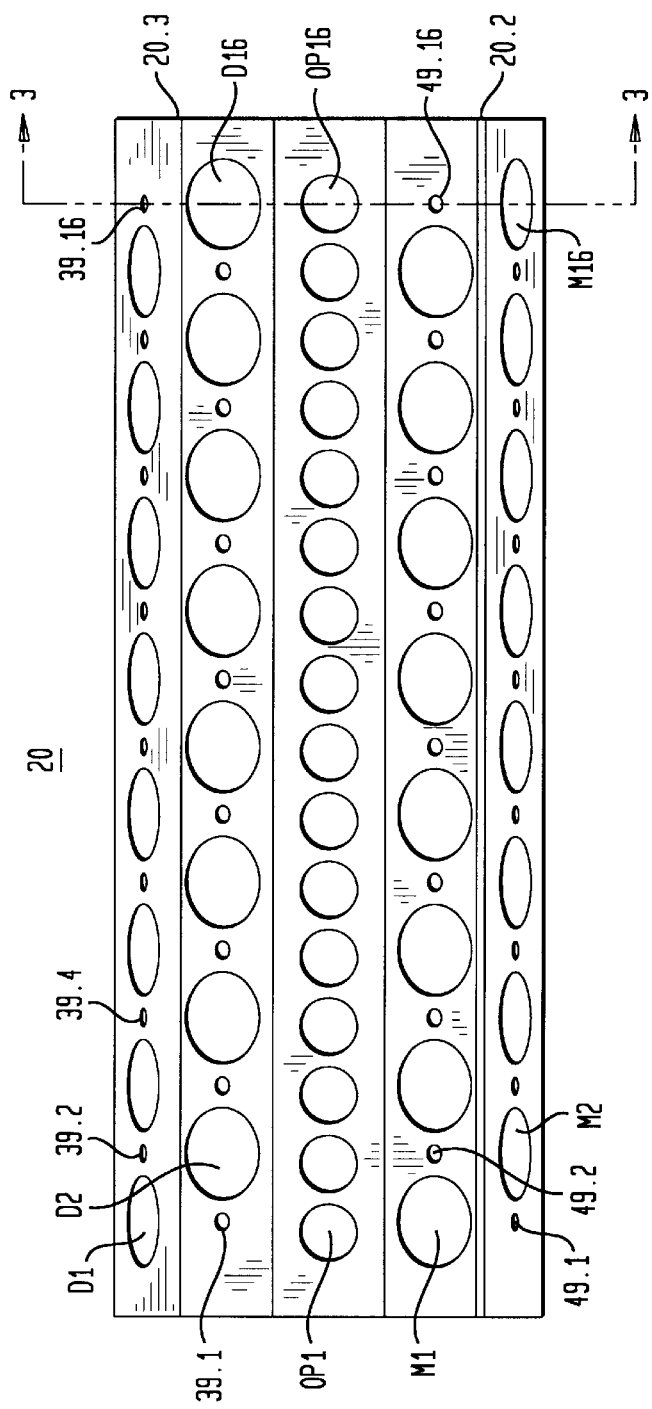
FIG. 2 is a top view of a scan head in accordance with one embodiment of our invention.
Figure 4:
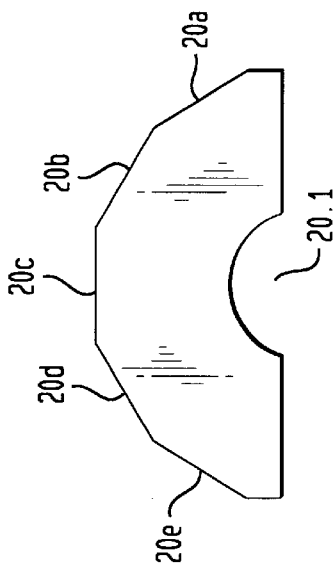
FIG. 4 is an end view of the scan head of FIG. 2.
Figure 3:
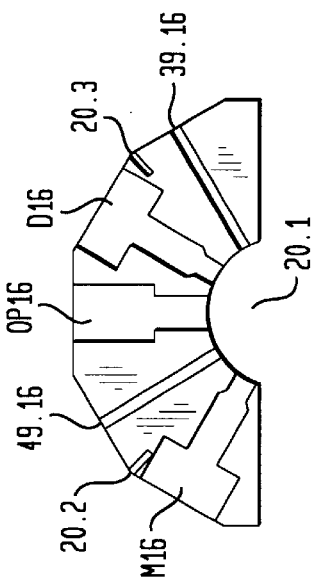
FIG. 3 is a cross-section taken along line 3—3 of FIG. 2.

The interleaving of the input ports with the output ports is depicted in FIG. 2. Illustratively, the odd numbered output ports D1, D3 etc. are interleaved on lateral facet 20a with even numbered input ports 39.2, 39.4 etc. Conversely, even numbered output ports D2, D4 etc. are interleaved on lateral facet 20b with odd numbered input ports 39.1, 39.3 etc. In a similar fashion, input ports $49n$ and output ports M$n$ are interleaved on lateral facets 20d and 20e. This interleaving of the ports on the one hand provides compactness to the design, and on the other hand aligns the monitor photodetectors to the pump fibers and the reflection photodetectors to the probe fibers. For example, as shown in FIG. 5, pump monitor PM16 is aligned to receive a portion of the pump signal which emanates from the pump fiber PPF16 and which is reflected from the wafer. Also, reflection detector RD16 is aligned to receive a portion of the probe signal which emanates from the probe fiber PRF16 and which is reflected from the wafer (i.e., the photoreflectance signal). The optical coupling between the fibers and the corresponding photodetectors is facilitated by lenses (e.g., GRIN lenses) L$n$ (n =1,2 . . . 16) positioned in the radial cavities D$n$ and M$n$ between the axial cavity 20.1 and the photodetectors. In addition, long wavelength pass filters F$n$ (n =1,2 . . . 16) may be likewise included in the radial cavities between the lenses and the axial cavity to block scattered pump light from reaching the reflection detectors where it can generate an unwanted background signal (i.e., noise).

Optionally, the scan head may also include one or more axial slots (e.g., 20.2 and 20.3 in FIGS. 2–3) into which printed circuit boards (e.g., PCB1 and PCB2 in FIG. 5) may be inserted. Such PCBs carry electronic circuits, typically operational amplifiers to amplify the signals from the reflection detectors. By placing the amplifiers as close as possible to the reflection detectors, parasitic capacitance is reduced and the signal-to-noise ratio of the amplifier output is increased.

Example

In this example we used the above described technique and apparatus to map the characteristics of a 2 inch diameter wafer. The pump signal was delivered to the scan head by single mode fibers 69, whereas the probe signal was delivered by 200 $\mu$m core diameter multimode fibers 79. However, the position and orientation of the fiber ends relative to the wafer surface was such that the probe and pump beam images overlapped and formed an approximately 500 $\mu$m image at each of N =16 spots. The scan head was stepped through 11 different positions on the wafer, taking PR measurements simultaneously at the 16 spots at each wafer position. Thus, a total of 176 PR measurements were made in about 5 hours. Using the prior art technique of making PR measurements at only one spot at a time, these measurements would have taken about 80 hours.

These PR measurements were obtained by tuning the monochromator wavelength from 0.7 eV to 1.4 eV and using InGaAs photodetectors to detect the probe beam and Si detectors to monitor the pump beam. The pump laser was a 7800 Angstrom diode laser which provided 0.2 mW of optical output power in each pump fiber. The pump laser was modulated at 200 Hz by modulating its drive current.

It is to be understood that the above-described arrangements are merely illustrative of the many possible specific embodiments which can be devised to represent application of the principles of the invention. Numerous and varied other arrangements can be devised in accordance with these principles by those skilled in the art without departing from the spirit and scope of the invention. In particular, although our scan head is depicted as addressing a linear array of N spots on wafer, it could readily be designed to address a two-dimensional array of M×N spots.

What is claimed is:

1. A method of making photoreflectance measurements simultaneously at N1 first spots on a wafer comprising the steps of generating N optical pump signals at a wavelength absorbed in the wafer, modulating the intensity of the pump signals, generating N optical probe signals at wavelengths tunable over a predetermined range, coupling the pump signals and the probe signals to a scan head which is positioned adjacent the wafer and which forms overlapping images of the signals at each of the N first spots on the wafer, thereby to generate N photoreflectance signals, one from each of the first spots on the wafer, photodetecting each of the N photoreflectance signals within the scan head, thereby generating N electrical signals corresponding to the photoreflectance signals, and providing the N electrical signals to a computer in order to calculate predetermined parameters of the wafer at each of the first spots.

2. The invention of claim 1 further including, after the measurements have been made on the N first spots, the step of moving the wafer relative to the scan head so as to make photoreflectance measurements on the wafer at N second spots.

3. The invention of claim 1 further including the step of photodetecting a portion of each of the N pump signals within the scan head, thereby to generate N electrical signals, and providing the N electrical signals to the computer for monitoring the intensity of the pump signals.

4. The invention of claim 1 wherein the images of each of said pump signals and its corresponding probe signal are approximately the same size.

5. The invention of claim 1 wherein the image of said probe signal is much smaller than the image of its corresponding pump signal.

6. Apparatus for making photoreflectance measurements simultaneously at N1 spots on a wafer comprising a scan head positionable in close proximity to the surface of the wafer, a pump source for generating N optical pump signals at a wavelength absorbed in the wafer, means for modulating the intensity of the pump source, a probe source for generating N optical probe signals at wavelengths tunable over a predetermined range, optical fibers for coupling the pump and probe signals to the scan head so as to form overlapping images of the pump and probe signals at each of the N spots on the wafer, thereby to generate N photoreflectance signals, one from each spot on the wafer, first photodetectors positioned within the scan head for converting the N photoreflectance signals to N corresponding electrical signals, and means for supplying the N electrical signals to a computer in order to calculate predetermined parameters of the wafer at each of the N spots.

7. The invention of claim 6 further including means for moving the wafer and/or the scan head relative to one another so as to make photoreflectance measurements at another N spots on the wafer.

8. The invention of claim 6 further including second photodetectors located within the scan head for converting a portion of the pump signals to corresponding electrical signals and means for coupling the electrical signals to the computer for monitoring the intensity of the pump signals.

9. The invention of claim 8 wherein said scan head comprises a semi-cylindrical body having an axial cavity which overlays the N spots and having a plurality of radial cavities in communication with the axial cavity, said radial cavities including a first group for receiving optical fibers carrying said pump signals, a second group for receiving optical fibers carrying said probe signals, a third group for receiving the first photodetectors and a fourth group for receiving the second photodetectors.

10. The invention of claim 9 wherein said groups are interleaved with one another.

11. The invention of claim 10 wherein the cavities of said first and third groups are interleaved with one another, and the cavities of said second and fourth groups are interleaved with one another.

12. The invention of claim 11 wherein the outer surface of said scan head has a plurality of axial facets in which said cavities are formed, the cavities of said first and third groups being formed in two of said facets, and the cavities of said second and fourth groups being formed in a different two of said facets.

13. The invention of claim 10 wherein each of said radial cavities has an axis which passes through the central axis of the semi-cylindrical body and said N spots are disposed along said central axis.

14. The invention of claim 6 wherein the images of each of said pump signals and its corresponding probe signal are approximately the same size.

15. The invention of claim 6 wherein the image of said probe signal is much smaller than the image of its corresponding pump signal.

* * * * *